UUnited States Patent [19]

Fiege et al.

[11] Patent Number: 5,659,088
[45] Date of Patent: Aug. 19, 1997

[54] PROCESS FOR THE PREPARATION OF 4-FLUOROTHIOPHENOL

[75] Inventors: Helmut Fiege; Ferdinand Hagedorn, both of Leverkusen; Wolfgang Eymann, Köln; Otto Neuner, Bergisch Gladbach; Herbert Müller, Kreuzau, all of Germany

[73] Assignee: Bayer Aktiengesellschaft, Leverkusen, Germany

[21] Appl. No.: 456,839

[22] Filed: Jun. 1, 1995

[30] Foreign Application Priority Data

Jun. 15, 1994 [DE] Germany ............ 44 20 777.8

[51] Int. Cl.⁶ .................. C07C 319/02; C07C 319/14
[52] U.S. Cl. ........................................ 568/65
[58] Field of Search ............................... 568/65

[56] References Cited

U.S. PATENT DOCUMENTS 4,209,469  6/1980  Thies et al. .

FOREIGN PATENT DOCUMENTS 0002755  7/1979  European Pat. Off. .
1816902  7/1970  Germany .
1222768  2/1971  Germany .
3302647  8/1984  Germany .
3304054  8/1984  Germany .
4022477  1/1992  Germany .

OTHER PUBLICATIONS

Chemical Abstracts, vol. 51, N. 22, Abstract No. 17793 (d), (1957).
A. Ookawa, et al., Synthetic Communications, vol. 16, No. 7, pp. 819–825, (1986).
Chem. Ber., vol. 86, p. 179 (1953).
A. Nose, et al., Chem. Pharm. Bull., vol. 35, pp. 1770–1776 (1987).

Primary Examiner—Gary Geist
Assistant Examiner—Jean F. Vollano
Attorney, Agent, or Firm—Sprung Horn Kramer & Woods

[57] ABSTRACT

4-Fluorothiophenol is obtained in outstanding purifies and yields if 4-fluorobenzenesulphonyl chloride is reacted with sodium hydrogen sulphite solution to give a solution of sodium 4-fluorobenzenesulphinate, this solution is reduced with sulphur dioxide to give 4,4'-difluorodiphenyl disulphide and finally this is reacted with sodium borohydride in a water-miscible inert organic solvent to give 4-fluorothiophenol (sodium salt). Free 4-fluorothiophenol can be isolated from the sodium salt solution by acidification.

10 Claims, No Drawings

PROCESS FOR THE PREPARATION OF 4-FLUOROTHIOPHENOL

The present invention relates to a process having a specific combination of measures for the preparation of pure 4-fluorothiophenol with high yield.

It is known to prepare 4-fluorothiophenol by reduction of 4-fluorobenzenesulphonyl chloride with zinc dust/sulphuric acid. The yield in this case is 72% of theory (Chem. Ber. 86, 179 (1953)). This process is little suited for an industrial procedure since a zinc-containing effluent arises. In addition, the reduction of substituted or unsubstituted benzenesulphonyl chlorides with sodium sulphite to give the corresponding sodium benzenesulphinates is known. In these cases, after reduction has been completed, the sodium salt of the sulphinic acid is usually isolated (see FIAT Final Report 949, pp. 23 and 24 and DE-A 3 302 647, Example 17). The yield of sulphinate is 80% in this case. According to the process DE-A 1 816 902, the reduction of aromatic sulphonyl chlorides with sodium sulphite to give sulphinic acid and the subsequent reduction with $SO_2$ of the acidified sulphinic acid solution successfully produces aromatic disulphides with good yields without the isolation of intermediates. This procedure is oriented to the preparation of aromatic disulphides which can be separated off in a crystalline state at the end. However, 4,4'-difluorodiphenyl disulphide is a product liquid at room temperature and therefore cannot be prepared in such a manner.

In the preparation of 4,4'-difluorodiphenyl disulphide, the acidification of the sulphinate solution is associated with an increase in density of the water phase which then gives an emulsion which is difficult to separate. Furthermore, an unnecessarily great amount of salt is generated as waste.

Hydrogenation processes for the reduction of aromatic sulphonyl chlorides and aromatic disulphides with hydrogen on noble metal catalysts are also known. High hydrogen pressures of up to 150 bar and temperatures up to 150° C. are disadvantageous in this case (see e.g. EP-A 2 755).

The reduction of 4-chlorobenzenesulphonyl chloride with sodium borohydride in tetrahydrofuran leads to a mixture of 4,4'-dichlorodiphenyl disulphide and 4-chlorothiophenol with a yield of approximately 40%. Per mol of sulphonyl chloride, a high excess of sodium borohydride must be used (see Chem. Pharm. Bull. 35, 1770 (1987)).

The reduction of aromatic disulphides with sodium borohydride is also known. In this case, according to Synth. Commun. 16, 819–825 (1986), a solvent mixture of tetrahydrofuran and methanol is necessary in order to achieve good yields. The use of only one solvent leads to poor yields of thiophenols. Moreover, the mount of sodium borohydride required in this process, at 2.5 mol per mol of disulphide is extraordinarily high. It must be taken into account that 1 mol of sodium borohydride contains 8 reducing equivalents.

There is therefore stir the requirement for an industrially simple process for the preparation of 4-fluorothiophenol in which, starting from 4-fluorobenzenesulphonyl chloride, the individual synthesis steps proceed with good yields and the above-described disadvantages of other processes can be substantially avoided.

It has now been found that 4-fluorothiophenol can be prepared in an advantageous manner if 4-fluorobenzenesulphonyl chloride is first reacted with sodium hydrogen sulphite solution to give a solution of sodium 4-fluorobenzenesulphinate, then this solution is reduced with sulphur dioxide to give 4,4'-difluorodiphenyl disulphide and this is finally reacted with sodium borohydride in a water-miscible inert organic solvent to give 4-fluorothiophenol (sodium salt). 4-Fluorothiophenol can be isolated from this sodium salt solution after distilling off the solvent, for example by acidifying the solution, separating off the organic phase forming and if appropriate purifying still further.

The process according to the invention can be carried out as a one-pot synthesis and can be illustrated by the following formula diagram:

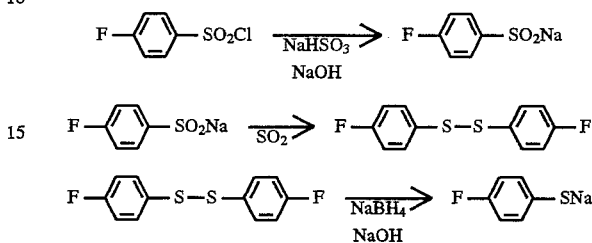

The starting material which serves for the process is 4-fluorobenzenesulphonyl chloride. This can be prepared e.g. in a known manner, for example by sulphochlorination of fluorobenzene. It is advantageous to use in the process according to the invention 4-fluorobenzenesulphonyl chloride which has been freed from 2-fluorobenzenesulphonyl chloride, e.g. by fractional distillation or fractional crystallization.

In the first stage of the process according to the invention, e.g. the 4-fluorobenzenesulphonyl chloride can be introduced in molten form (melting point 38° C.) into a given aqueous solution of sodium hydrogen sulphite. It is generally advantageous to use the sodium hydrogen sulphite in excess, e.g. in excess of 5 to 10 mol %. It is further advantageous to use the sodium hydrogen sulphite in a not too concentrated solution or to add water. For example, a 5 to 20% strength by weight sodium hydrogen sulphite solution is highly suitable. After addition of 4-fluorobenzenesulphonyl chloride is complete, the mixture can be allowed to continue reacting e.g. for a further 1 to 3 hours. It is advantageous to keep the pH in the range from 6.3 to 6.7 before and during the reaction, which can be achieved, for example, by addition of aqueous sodium hydroxide solution. The pH is preferably kept in the range from 6.4 to 6.6. The reaction temperature is advantageously chosen to be above the melting point of 4-fluorobenzenesulphonyl chloride, since the sulphonyl chloride reacts only very slowly in crystalline form. For example, temperatures in the range from 35° to 80° C. are used, preferably those in the range from 40° to 80° C. The reaction generally proceeds quantitatively and with a selectivity of virtually 100%.

In view of the subsequent reaction of the resulting 4-fluorobenzenesulphinate solution with sulphur dioxide, acidification of the solution is highly disadvantageous. By addition of acid, the pressure during the reduction with sulphur dioxide would be undesirably increased, the specific gravity of the water phase would increase after the reaction is completed to the extent that a phase separation from the 4,4'-difluorodiphenyl disulphide arising in the liquid state would be made unnecessarily more difficult and, because a two-phase mixture would already be formed on the addition of acid, the handling behaviour of which is less favourable in the following reaction than that of a homogeneous solution.

For the reaction with sulphur dioxide, expediently, the 4-fluorosulphinate solution is used as is present after the first stage of the process according to the invention. Further processing can also be carried out in the same reaction vessel.

It is generally advantageous to use sulphur dioxide in a stoichiometric amount or in excess, e.g. 1.5 to 1.7 mol per mol of 4-fluorobenzenesulphonyl chloride. Sulphur dioxide can be used in liquid form or as a gas.

The reaction temperature during the reduction of the sulphinate solution can be e.g. in the range from 20° to 170° C. It is advantageous to begin this reduction at relatively low temperature, e.g. at 20° to 50° C., and to finish it at a relatively elevated temperature, e.g. at 120° to 160° C. It is frequently advantageous to maintain a relatively higher temperature in the reaction mixture for 2 to 10 hours. During this reduction, the pressure can rise, for example, up to 10 bar. Pressures between 1 and 5 bar are preferably employed.

After the reduction, 4,4'-difluorodiphenyl disulphide arises as a yellow oil, e.g. at approximately 30° C. The aqueous (upper) phase can easily be separated off from the lower disulphide phase. It is advantageous to free the disulphide from residues of adhering acids and salts with a subsequent wash with water. The yield of 4,4'-difluorodiphenyl disulphide is up to 98%, based on 4-fluorobenzenesulphonyl chloride.

The 4,4'-difluorodiphenyl disulphide is then converted to 4-fluorothiophenol (sodium salt) in a water-miscible inert organic solvent. For this purpose, e.g., the disulphide situated in the reaction vessel can be dissolved in a water-miscible organic solvent inert towards sodium borohydride and enough aqueous sodium hydroxide-containing solution of sodium borohydride can be added so that the desired reaction temperature is maintained. The reaction temperature can be e.g. between room temperature and the boiling point of the respective solvent or the boiling point of the azeotrope of water and the respective solvent. The reaction is preferably allowed to proceed under reflux in order to be able to remove the heat of reaction in this manner. Temperatures in the range from 60° to 100° C. are preferred. 1.8 to 2.2 mol of NaOH can be used, for example, per mol of 4,4'-difluorodiphenyl disulphide.

After addition of the sodium borohydride is completed, it is advantageous to continue stirring the mixture for a further 1 to 5 hours. A clear and virtually colourless solution is then generally present which contains 4-fluorothiophenol as sodium salt. This solution can be e.g. worked up by acidifying it with mineral acids, preferably with hydrochloric acid, separating off the lower 4-fluorothiophenol phase formed and carrying out further purification after removing contaminating salts by washing with water and by incipient distillation or complete distillation. In this manner 4-fluorothiophenol can be obtained e.g. in purities of over 99% and at yields of up to 88% (based on 4,4'-difluorodiphenyl disulphide).

Sodium borohydride can be used, e.g, in amounts of 0.25 to 1.0 mol per mol of disulphide. An excess of sodium borohydride is preferably used, for example 0.3 to 0.6 mol per mol of disulphide. Greater excesses are not advantageous from the industrial viewpoint and are not expedient out of economic considerations.

Inert water-miscible organic solvents which may be used are, for example, lower aliphatic alcohols such as methanol, ethanol and isopropanol and tetrahydrofuran, diglyme and dimethylformamide. Preference is given to solvents which can be easily separated off from the aqueous solution, e.g. by distillation. Methanol or isopropanol is particularly preferably used.

The amount of solvent is advantageously of the size such that the reaction mixture forms a homogeneous phase during the addition of sodium borohydride and during the entire reduction operation.

The solvent used in the reduction with sodium borohydride can be reused (pure or as an azeotrope with water) after being distilled off.

By acidifying the aqueous sodium 4-fluorothiophenolate solution, e.g. with concentrated hydrochloric acid to a pH of 0.5 to 2.5, 4-fluorothiophenol can be obtained and separated off as a clear lower phase. By incipient distillation, highly pure 4-fluorothiophenol can be obtained as a clear, colourless liquid.

The content of the isolated 4-fluorothiophenol is frequently over 99%. Contamination by 2-fluorothiophenol may be avoided by using, in the reduction of 4-fluorobenzenesulphonyl chloride, a material from which the 2-isomer has been separated off.

4-Fluorothiophenol is an important intermediate, e.g. for the preparation of pharmaceutical active substances (see EP-A 100 172).

The following Examples illustrate the invention.

EXAMPLES

Example 1

345 ml of aqueous sodium hydrogen sulphite solution (40% strength) and 1,050 ml of water were placed in a pressure vessel under nitrogen and adjusted to a pH of 6.5 with 56 ml of sodium hydroxide solution (44.8% strength). During this, the mixture was heated to 40° C. 315.8 g of 4-fluorobenzenesulphonyl chloride were then added dropwise at 40° to 45° C. and the pH was held at 6.5 by simultaneous dropwise addition of 225 ml of sodium hydroxide solution (44.8% strength). After addition of the 4-fluorobenzenesulphonyl chloride was completed, the mixture continued to be stirred for a further 2 hours.

After flushing twice with nitrogen, 118 ml of sulphur dioxide in liquid form were forced into the pressure vessel at room temperature. The mixture was heated to 135° C. in the course of 3 hours with stirring and then continued to be stirred for 5 hours at this temperature. During the reaction the pressure was approximately 5 bar.

After the reaction was completed, the mixture was cooled to 30° C., the pressure vessel was depressurized, the aqueous phase was separated off and the remaining disulphide phase was washed with water. The yield of 4,4'-difluorodiphenyl disulphide was 98%, based on 4-fluorobenzenesulphonyl chloride used.

Example 2

187.4 g of 4,4'-difluorodiphenyl disulphide were dissolved in 650 ml of isopropanol and 90 ml of water. The solution was heated to reflux temperature (80° to 82° C.) under nitrogen and at this temperature a solution of 15.7 g of $NaBH_4$ (98% strength) in aqueous sodium hydroxide solution was added dropwise to the mixture in the course of one hour. The sodium hydroxide solution had been obtained from 92 ml of 45% strength sodium hydroxide solution and 400 ml of water. The reaction mixture continued to be stirred for 2 hours. The initially yellow coloration had then completely disappeared. The isopropanol was then completely distilled off, at the same time 700 ml of water were added. The solution was cooled to 60° C. and adjusted to a pH of 1 by addition of concentrated hydrochloric acid (approximately 160 ml), a lower phase separating off which essentially contained 4-fluorothiophenol. By incipient distillation of the separated-off lower phase, an anhydrous, clear 4-fluorothiophenol (purity: 98.7%) was obtained in a yield of 74% of theory.

Example 3

186.4 g of 4,4'-difluorodiphenyl disulphide were dissolved in 325 ml of isopropanol and 45 ml of water and then reduced with an NaBH$_4$ solution as described in Example 2 and the reaction mixture was worked up as described there. 99.2% pure 4-fluorothiophenol was obtained in a yield of 94.3% of theory. By extraction of the water phase, a further 4.2% of 4-fluorothiophenol could be isolated which then gave an overall yield of 98.5%.

Example 4

195 g of 4,4'-difluorodiphenyl disulphide were dissolved in 650 ml of methanol and 90 ml of water and reduced in a similar manner to that described in Example 2 by dropwise addition of a solution of 16.3 g of NaBH$_4$ in 370 ml of water and 140 g of a 43.8% strength aqueous sodium hydroxide solution at 70° to 78° C. Work up and isolation were likewise carried out in a similar manner to Example 2. 4-Fluorothiophenol was obtained in a purity of 99.5% and in a yield of 95% of theory. By extraction of the water phase, a further 3.2% of 4-fluorothiophenol could be isolated so that the overall yield was 98.2%.

Example 5

The reduction of 190.8 g of 4,4'-difluorodiphenyl disulphide was carried out in accordance with Example 4, but instead of methanol, 650 ml of tetrahydrofuran were used. 4-Fluorothiophenol was obtained in a yield of 95.1% of theory, and a further 3.1% was obtained by extraction of the water phase, so that the overall yield was 98.5%. The purity of the product was 99.6%.

Example 6

194 g of 4,4'-difluorodiphenyl disulphide were placed in 650 ml of isopropanol and 90 ml of water and reduced by dropwise addition of a solution of 16.2 g of NaBH$_4$ in 370 ml of water and 139.3 g of 43.8% strength aqueous sodium hydroxide solution (94.8 ml) at 50° C. in the course of 2 hours and continuing to stir the mixture forming for a further 10 hours and leaving the solution overnight. The work up and isolation of the 4-fluorothiophenol was carded out as described in Example 2. 4-Fluorothiophenol was obtained in a yield of 93.2% of theory and a further 6.5 g were obtained by extraction, so that the overall yield was 96.5%. The purity of the product was 99.4%.

What is claimed is:

1. A process for preparing the sodium salt of 4-fluorothiophenol or 4-fluorothiophenol itself, said process comprising the following steps:

(A) reacting 4-fluorobenzene sulphonyl chloride with sodium hydrogen sulphite solution to yield a solution of sodium 4-fluorobenzensesulphinate;

(B) reducing 4-fluorobenzenesulphinate with sulphur dioxide to yield 4,4'-difluorophenyl disulphide;

(c) reacting 4,4'-difluorophenyl disulphide with sodium borohydride in a water-miscible inert organic solvent to yield the sodium salt solution of 4-fluorothiophenyl;

and, optionally, if 4-fluorothiophenol itself is desired, then:

(D) converting the sodium salt solution of 4-fluorothiophenol to 4-fluorothiophenol itself by acidification.

2. The process of claim 1, in which 4-fluorobenzenesulphonyl chloride is used which has been freed from 2-fluorobenzenesulphonyl chloride.

3. The process of claim 1, in which 4-fluorobenzenesulphonyl chloride is introduced in molten form at 35° to 80° C. into a given aqueous sodium hydrogen sulphite solution, the pH is kept in the range from 6.3 to 6.7 and when the addition of the 4-fluorobenzenesulphonyl chloride is complete, the mixture is allowed to continue reacting for a further 1 to 3 hours.

4. The process of claim 1, in which the sodium hydrogen sulphite is used in an excess of 5 to 10 mol %.

5. The process of claim 1, in which the solution of 4-fluorobenzenesulphinate obtained in the first stage is reacted in the same reaction vessel with 1.5 to 1.7 mol of sulphur dioxide per mol of 4-fluorobenzenesulphonyl chloride at 20° to 170° C. at a pressure up to 10 bar in the course of 2 to 10 hours.

6. The process of claim 1, in which the 4,4'-difluorodiphenyl disulphide obtained after the reduction with sulphur dioxide is washed with water and then, in a water-miscible organic solvent inert towards sodium borohydride, is converted to the sodium salt of 4-fluorothiophenol by addition of an aqueous sodium hydroxide-containing solution of sodium borohydride.

7. The process of claim 1, in which 1.8 to 2.2 mol of NaOH and 0.25 to 1.0 mol of sodium borohydride are used per mol of 4,4'-difluorodiphenyl disulphide and the reaction is carried out at a temperature in the range from 60° to 100° C.

8. The process of claim 1, in which the water-miscible inert organic solvent used is a low aliphatic alcohol, tetrahydrofuran, diglyme or dimethylformamide.

9. The process of claim 1, in which after the reduction with sodium borohydride the solvent is distilled off and by acidification of an aqueous sodium 4-fluorothiophenolate solution 4-fluorothiophenol is obtained.

10. The process of claim 1, in which the 4-fluorothiophenol obtained is further purified by incipient distillation.

* * * * *

UNITED STATES PATENT AND TRADEMARK OFFICE
CERTIFICATE OF CORRECTION

PATENT NO. : 5,659,088
DATED : August 19, 1997
INVENTOR(S) : Fiege, et al.

It is certified that error appears in the above-indentified patent and that said Letters Patent is hereby corrected as shown below:

Title Page     U.S. PATENT DOCUMENTS: Insert -- 4,006,186, 1/1997, Engels et al. --

Title Page     ABSTRACT: Line 1, delete " purifies " and substitute -- purities --

Signed and Sealed this

Ninth Day of December, 1997

Attest:

BRUCE LEHMAN

Attesting Officer     *Commissioner of Patents and Trademarks*